United States Patent [19]

Kopp

[11] E Re. 29,346

[45] Reissued Aug. 9, 1977

[54] SINGLE NEEDLE DIALYSIS

[75] Inventor: Klaus F. Kopp, Kirchseeon, Germany

[73] Assignee: Vital Assists, Inc., Salt Lake City, Utah

[21] Appl. No.: 610,043

[22] Filed: Sept. 3, 1975

Related U.S. Patent Documents

Reissue of:

[64] Patent No.: 3,756,234
Issued: Sept. 4, 1973
Appl. No.: 149,905
Filed: June 4, 1971

[51] Int. Cl.[2] ..... A61M 5/00; A61M 1/03

[52] U.S. Cl. ..... 128/214 R; 128/214 E; 210/90

[58] Field of Search ..... 128/DIG. 3, 214 R, 214 B, 128/214 E, 214 F, 214.2, 214.4, 213, 227; 210/90, 321 B

[56] References Cited

U.S. PATENT DOCUMENTS

| | | | |
|---|---|---|---|
| 2,474,665 | 6/1949 | Guarino | 128/DIG. 3 |
| 2,625,932 | 1/1953 | Salisbury | 128/214.2 |
| 2,659,368 | 11/1953 | Gibbon et al. | 23/258.5 |
| 2,721,732 | 10/1955 | Melrose | 23/258.5 |
| 2,927,582 | 3/1956 | Berkman et al. | 23/258.5 |
| 3,098,480 | 7/1963 | Worthington | 128/214 B |
| 3,416,664 | 12/1968 | Kumme et al. | 210/321 B |

OTHER PUBLICATIONS

Guarino et al. - Science, vol. 115, Mar. 1952, pp. 285-288.
Shaldon et al. - Lancet - Oct. 19, 1963, p. 815.
Twiss - Lancet - Nov. 1964, No. 7369, p. 1106.
Piazza et al. - Trans. Amer. Soc. Art. Inter. Orgs., vol. X, Apr. 1964, pp. 136-138.

*Primary Examiner*—Dalton L. Truluck
*Attorney, Agent, or Firm*—Fitzpatrick, Cella, Harper & Scinto

[57] ABSTRACT

Method and apparatus for extracorporeally dialyzing the blood of a patient with only a single venipuncture including withdrawing blood from the patient through the venipuncture and forcing the blood along an arterial path to a dialyzer. Blood emerging from the dialyzer is then conducted along a venous path again to the venipuncture. The pressure is monitored in the extracorporeal system to trigger occluding devices which alternately open and close the arterial and venous paths so that undialyzed blood is taken from the patient and dialyzed blood is injected into the patient. The apparatus includes clamps actuated by a pressure monitor to alternately obstruct the arterial and venous paths. A blood pump may be controlled to operate as one of the clamps. In an alternative embodiment, blood is circulated at a comparatively high flow rate throughout the system. A clamp is provided in one of the arterial or venous lines, said clamp being controlled by a pressure monitor. When the clamp is closed, a pressure differential is developed between the extracorporeal system and the patient so that a volume of blood is exchanged between the system and the patient.

4 Claims, 10 Drawing Figures

INVENTOR.
KLAUS F. KOPP
BY H. Ross Workman
ATTORNEY

INVENTOR.
KLAUS F. KOPP
BY H. Ross Starkey
ATTORNEY

INVENTOR.
KLAUS F. KOPP
BY H. Ross Starkman
ATTORNEY

SINGLE NEEDLE DIALYSIS

Matter enclosed in heavy brackets [ ] appears in the original patent but forms no part of this reissue specification; matter printed in italics indicates the additions made by reissue.

BACKGROUND

1. Field of the Invention

The invention relates to extracorporeal hemodialysis and more particularly to method and apparatus for dialyzing a patient's blood with a single venipuncture or cannulation.

2. The Prior Art

Historically, kidney diseases have been of critical concern to human life. Many kinds of kidney diseases interfere with the function of the kidney such that the kidney ceases to remove waste and excess water from the blood. When the kidney is sufficiently impaired that a large portion of the waste products and water are not removed from the blood, the life of the patient cannot be preserved unless a way is provided for artifically performing the function of the impaired kidney. Many new developments have come to light which perform the function of the impaired kidney extracorporeally. For example, see copending U.S. patent application Ser. No. 106,184, filed Jan. 13, 1971. Nevertheless, even with the existing improvements in extracorporeal kidney apparatus, the same general procedure is used for dialyzing patients' blood that was used very early in the treatment of kidney disease.

For example, the most commonly accepted practice for dialyzing a patient's blood extracorporeally requires the surgical creation of a subcutaneous, arterio-venous fistula. Thereafter, the subcutaneous venous system dilates secondary to the increase of blood flow derived from the artery to the vein through the fistula. Sufficient blood flow for dialysis is then obtainable by venipuncture with large bore needles. Normally, two hollow needles or cannulas with an internal stylet or trocar are used to perform two venipunctures on the patient so that two blood-communication sites exist simultaneously in the patient. Conventionally, blood is withdrawn from one of the punctured blood vessels, forced through a hemodialyzer and thereafter forced into the other.

The aforementioned procedure has been found to have serious disadvantages both to the patient and to the attending physicians and technicians. The problems are particularly aggravated because most patients requiring extracorporeal hemodialysis must undergo treatment as frequently as three to seven times per week. This means that if every venipuncture were completely successful, a patient would need to undergo from 6 to 14 venipunctures or cannulations each week.

It is well-known that the duration and well-function of a fistula created by venipuncture is inversely related to the number of venipunctures. Tissue repeatedly subjected to the trauma of venipuncture is much more susceptible to thrombophlebitis, paravascular hemorrhage, clotting and infection. In fact, it is commonly found in patients who have experienced a number of venipunctures, that the tissues surrounding the most accessible veins develop large hematomas which obscure the veins making successful venipuncture extremely difficult because of insufficient blood flow in the damaged blood vessels.

Also contributing to the problem is the fact that once one successful venipuncture is made and blood is allowed to flow from the patient's body toward a hemodialyzer, the blood volume in the patient's body is reduced making the second venipuncture very difficult. Historically, it has been found that while most skilled physicians or technicians are able to perform the first venipuncture with little difficulty, frequently a plurality of attempts is necessary before a second venipuncture can be performed on the same patient.

Additionally, while the pain and discomfort suffered by the patient is understandable, the multiple attempts at venipuncture often necessary to place the second needle results in increasing apprehension, and anxiety on the part of both the patient and the physician or technician attending the patient further reduces the likelihood of successful venipuncture.

BRIEF DESCRIPTION AND OBJECTS OF THE INVENTION

The present invention, including novel method and apparatus, reduces patient trauma and tissue damage by accommodating extracorporeal hemodialysis with a single venipuncture. Generally, once the venipuncture has been performed, blood is conducted away from the venipuncture site through one branch of a bifurcated blood path. The bifurcation is located next to the needle connector to keep the resulting deadspace as small as possible. The blood is forced through the extracorporeal hemodialyzer and thereafter through the other branch of the bifurcated flow path again to the venipuncture site. The method using the single venipuncture is made possible by alternating the blood flow into and out of the patient at the venipuncture site. A unidirectional pulsatile blood flow thrugh the dialyzer is established by alternate occlusion of the branches of the bifurcated blood path. For example, with one branch occluded, blood is withdrawn from the patient through the other branch into the hemodialyzer. The other branch is then occluded and the blood is forced through the one branch again into the patient.

It is, therefore, a primary object of the present invention to provide an improved method of extracorporeal hemodialysis using a single venipuncture for each treatment.

It is another primary object of the present invention to provide improved apparatus facilitating extracorporeal hemodialysis with a single venipuncture.

Another valuable object of the present invention is to provide an improved system for single needle dialysis for providing unidirectional pulsatile flow from the patient, to an extracorporeal dialyzer and again to the patient.

One still further and no less important object of the present invention is to provide a novel method of forcing blood through an extracorporeal system at an accelerated rate with periodic exchanges of blood volumes between the patient and the system.

These and other objects and features of the present invention will become more fully apparent from the following description and appended claims taken in conjunction with the accompanying drawings.

DETAILED DESCRIPTION OF THE PREFERRED EMBODIMENTS

Reference is now made to the [*prefered*] *preferred* embodiments of the invention as illustrated in the figures, like parts being designated with like numerals throughout.

Figure 1:
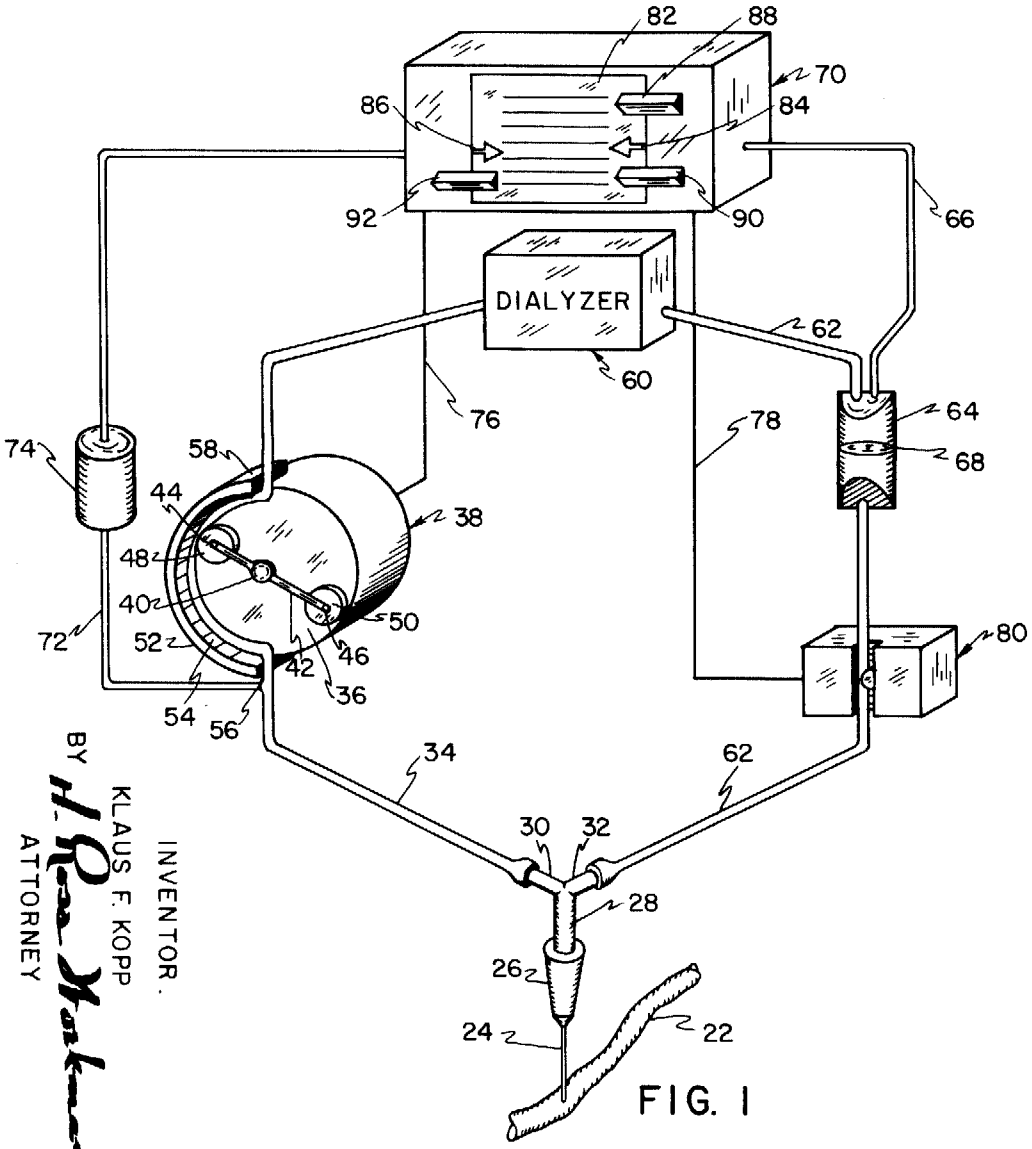
FIG. 1 is a schematic perspective illustration of a presently preferred system for dialyzing a patient's blood using a single venipuncture.

The System of FIG. 1

Referring now to FIG. 1, a blood vessel 22 is illustrated as having been penetrated by a hollow cannula 24. Preferably, the penetration has been performed according to any suitable technique such as venipuncture. The cannula 24 may be of any suitable type and may be made of radiopaque Teflon. One suitable cannula has been found to be the Angiocath intravenous placement unit manufactured by Deseret Pharmaceutical Company, Inc. Sandy, Utah. A 14-gauge catheter having a length of between one and two inches has been found to be most effective. Nevertheless, it is also presently preferred to use a hollow needle or any other suitable hollow instrument which can be effectively placed within a vein. In this specification, cannula means any hollow tubing which can be placed in a patient's blood vessel.

In the illustrated embodiment, the cannula 24 has an outwardly-tapered female or luer fitting 26 which is securely joined to a bifurcated coupling 28. Coupling 28 has an arterial branch 30 and a venous branch 32, arterial branch 30 being press-fit into a rubber or plastic tube 34. Tube 34 will hereinafter be referred to as the arterial line 34.

Arterial line 34 is situated over the face 36 of a blood pump generally designated 38. Blood pump 38 is conventional and normally includes a rotatable shaft 40 upon which is mounted a transverse bar 42. The bar 42 has, at its respective ends 44 and 46 rotatable cylinders 48 and 50.

Approximately one-half of the circular path traversed by the cylinders 48 and 50 is bordered by a semi-circular track 52. The arterial line 34 is caused to follow the inside surface 54 of the track 52. Thus, as the cylinders 48 and 50 traverse their circular path about the axis of shaft 40, the arterial line 34 will be squeezed between the respective cylinders and the track 52. Conventionally, the bar 42 rotates clockwise around the shaft 40 so that the squeezed portion of the arterial line 34 is developed between the cylinder and the track 52 at the leading end 56 of the track and progresses over the entire inside surface 54 of the track to the trailing end 58 thereof. As the squeezed portion of the arterial line 34 progresses over the inside surface of the track 52, blood in the arterial line 34 is forced to the dialyzer generally designated 60. It can be appreciated that when the cylinder 48 reaches the trailing end 58 of the track 52, the cylinder 50 will engage the arterial line 34 at the leading end 56 so that a constant forward pressure is exerted on the blood to move from the blood vessel 22 to the dialyzer 60 as long as the pump is in operation.

Any suitable conventional dialyzer can be used with the present system. An example of one suitable dialyzer which could be used in the Coil EX-01 manufactured by Extracorporeal, Inc. Another suitable dialyzer is described in pending designated S. Pat. application Ser. No. 106,184, filed Jan. 13, 1971. Blood emerges from the dialyzer 60 in the venous line 62 which is press-fit onto the branch 32 of the coupling 28. Preferably, a bubble trap 64 is interposed in the venous line 62 to prevent bubbles from passing through the cannula 24 into the blood vessel 22. The bubble trap 64 may be any suitable conventional bubble trap such as that used with blood infusion apparatus.

A pressure conductor 66 is connected into the bubble trap 64 above the surface level 68 of the blood. Thus, pressure within the bubble trap 64 and venous line 62 is transmitted through the conductor 66 to a pressure monitor generally designated 70. Similarly, a pressure conductor 72 is connected into the arterial line 34 so as to transmit pressure from the arterial line 34 to the pressure monitor 70. It is presently preferred that an accumulator 74 be interposed in the conductor 72 so as to provide an air pillow between the blood in arterial line 34 and the pressure monitor 70. The pressure monitor 70 is connected by electrical conductors 76 and 78 to the blood pump 38 and an electrically-operated clamp 80, respectively.

The Pressure Monitor

In order to make single venipuncture hemodialysis possible, the pressure monitor 70 has multiple set points. Furthermore, although a single pressure monitor is illustrated in FIG. 1, it may be desirable to have a plurality of pressure monitors to insure safety in the system. A variety of suitable conventional pressure monitors are commercially available, one suitable monitor being manufactured by Cambridge Instrument Corporation of Great Britain. Most conventional pressure monitors are operated with pressure diaphragms or the like. However, the illustrated pressure monitor 70 uses a mercury manometer system. For ease of illustration, only pressure monitor 70 will be described.

The pressure monitor 70 has a calibrated bezel 82 with indicia thereon representing, for example, millimeters of mercury. An indicator 84 is controlled by venous line pressure in conductor 66 so that when the venous line pressure in conductor 66 rises, the indicator 84 rises to indicate the pressure in millimeters of mercury (mm Hg). Similarly, when the pressure in conductor 66 drops, the indicator 84 drops to represent the decreasing pressure in millimeters of mercury. Another indicator 86 is controlled by the pressure in line 72 to indicate the pressure in the arterial line in millimeters of mercury.

Manually adjustable set points are determined by the position of markers 88, 90 and 92. For example, markers 88 and 90 respectively set the upper and lower limits of blood pressure in the venous line 62 as will be subsequently more fully described. Similarly, marker 92 will set the lower limit of the pressure in the arterial line 34. Preferably, the pressure range accommodated by the monitor 70 for measuring the pressure in venous line 62 is on the order of about zero to 300 mm Hg. The pressure range accommodated by the monitor 70 for indicating the pressure in arterial line 34 is preferably in a range on the order of about −150 to +200 mm Hg. Set point accuracy of the markers 88 have been found most desirably to be within ±5 mm Hg.

Figure 3:
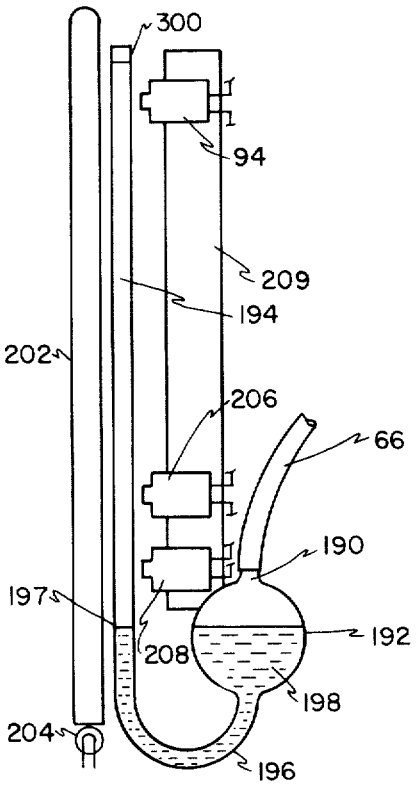
FIGS. 3 and 3a schematically illustrate internal components of a presently preferred pressure monitor.

Although a variety of pressure measuring systems could be used, it has been found that a mercury column manometer is both accurate and dependable for use in the pressure monitor 70. The mercury column manometer has the advantages of giving a continuous visual pressure indication and is also a familiar instrument to medical personnel. One presently preferred embodiment of the pressure monitor 70 is illustrated in FIG. 3. With reference to FIG. 3, the pressure conductor 66 is connected in pressure-tight relation to a hollow fitting 190 on a mercury reservoir 192. The reservoir 192 is integrally joined to an open column or tube 194 having a generally U-shaped intermediate segment 196 disposed beneath the reservoir 192. As can be appreciated by referring to FIG. 3, the upper level 197 of the mercury 198 will seek the level of the reservoir. Thus, the line 197, when even with the reservoir level, may be interpreted as the zero pressure point for the FIG. 3 embodiment. Preferably, the tube 194 is calibrated so that 300 mm Hg pressure is required to move the line 197 to the point 300.

A cylindrical rod 202 is provided adjacent the column 194, the rod 202 being formed of light illuminable plastic. An incandescent lamp or other suitable light source 204 is placed adjacent one end of the rod 202 and, when the light source 204 is illuminated, the entire rod 202 will become illuminated.

A plurality of photoelectric cells 94, 206 and 208 are disposed on the other side of the column 14 diametrally opposite the rod 202. The photocells 94, 206 and 208 are preferably shielded by structure (not shown) which prevents light from the rod 202 from reaching the photocell except through the column 194. The photocells may be mounted on a vertical rack 209 and are preferably vertically adjustable along the rack 209 by any suitable conventional adjusting structure (not shown).

In the operation of the apparatus of FIG. 3, as the mercury 198 advances in the column 194, the mercury will obstruct the light path between the rod 202 and the photocells 94, 206 and 208. More specifically, for example, when the mercury advances to the mark 200, the photocell 94 will be de-energized because light from the rod 202 will be obstructed by the mercury. Similarly, when the mercury advances below the position of the photocell 94, the photocell will be energized.

Figure 3A:
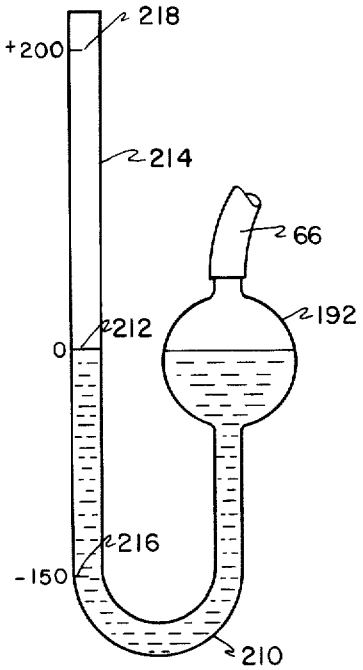

While the range of the column 194 in FIG. 3 is, for example, between 0 and 300 mm Hg, any suitable pressure reading is possible as is made clear from the schematic representation of FIG. 3a. In FIG. 3a, the U-shaped portion 210 is substantially elongated over the U-shaped portion 16 (FIG. 3), so that the zero point 212, where the mercury comes to rest with the level of mercury in the reservoir 192, is intermediate the length of mercury column 214. Thus, for example, the mercury level 212 may fluctuate between readings of approximately minus 150 mm Hg such as at point 216 to approximately 200 mm Hg at point 218.

Figure 2:
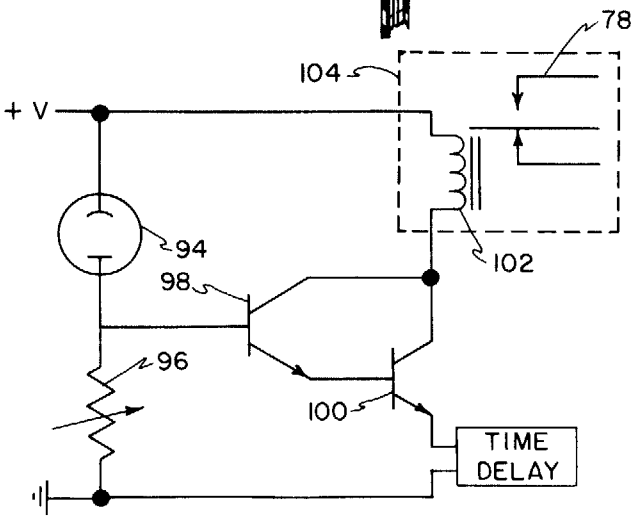
FIG. 2 is a schematic circuit diagram illustrating a presently preferred pressure monitor circuit.

The mercury column manometer, when used in conjunction with the photocell circuit illustrated in FIG. 2, provides for highly accurate set point determination. Referring more specifically to FIG. 2, photocell 94 is connected to a variable resistor 96 which is a threshold control to determine the sensitivity of the photocell 94. When photocell 94 is energized by the light source 202 (FIG. 3), the resulting signal will be amplified by stepped transistors 98 and 100 so as to energize relay drive 102. Relay driver 102 controls the operational state of relay 104 which, in turn, controls the function of solenoid clamp 80 (FIG. 1). When the pressure in venous line 62 is below the set point 88, the photocell 94 will be exposed to the light source thereby energizing relay driver 102 and switching the relay 104 to an "on" position to actuate the solenoid clamp 80 (FIG. 1). The clamp 80 then closes and occludes the venous line 62. With the venous line 62 occluded, the pressure in the line 62 will rise until the indicator 84 reaches the set point determined by marker 88. At that moment, the mercury 198 in column 194 (FIG. 3) will have risen sufficiently to obstruct the light from the light source 202 to the photocell 94 thereby turning the photocell 94 off. The relay driver 102 is then no longer energized and relay 104 is switched to the "off" position thereby opening the solenoid clamp 80. A conventional time delay circuit may be used to prevent for a predetermined time period re-actuation of relay 104 when the mercury drops to expose photocell 94 to the light source 202.

A separate solenoid circuit which may be substantially identical to that shown in FIG. 2 may be provided for each of the set points determined by markers 90 and 92. Additionally, if desired, a third set point (not shown in FIG. 1) may be provided to correspond to photocell 208 (FIG. 3) so as to act as a "safety low" set point which is normally slightly lower than the set point indicated by marker 90. Thus, in the event a membrane or coil in the dialyzer 60 ruptures, an instantaneous drop in pressure to the "safety low" set point will actuate the solenoid 80 to an open position and the pump 38 to stop to protect the patient.

Figure 4:
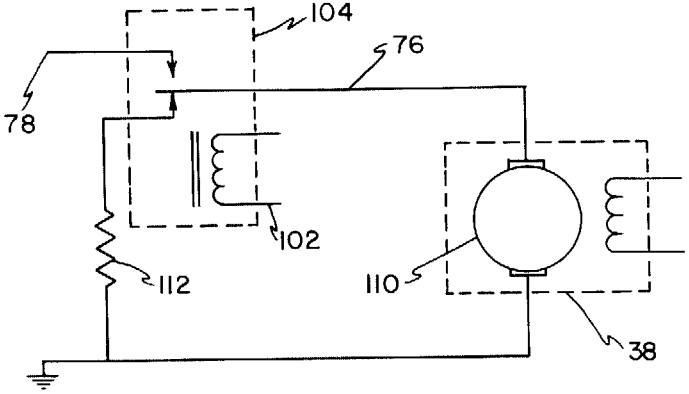
FIGS. 4 and 5 are schematic circuit diagrams respectively illustrating alternative embodiments which may be used with the system of FIG. 1 to control the operation of the blood pump.

In the system illustrated in FIG. 1, the pressure monitor 70 also controls the operation of the blood pump 38. Referring specially to FIG. 4, the relay 104, controlled by the photocell circuit illustrated in FIG. 2, is energized so that the relay driver 102 disconnects solenoid line 78 from the circuit. The solenoid 80 responds by clamping the venous line 62 closed. Simultaneously, the motor 38 is energized to draw blood from the venipuncture in blood vessel 22 and drive it toward the dialyzer 60. When the pressure [reises,] *rises,* as above described, the relay 104 will reverse to open the clamp 80 and stop the pump 38. Pump 38 thus functions as a second clamp.

It has been found that the blood pump 38 does not instantaneously stop when it is disconnected from the circuit by the pressure monitor 70 because of the moment of inertia of the blood pump motor. Accordingly, in the illustrated embodiment of FIG. 4, the armature 110 of the motor 38 is connected through a resistor 112 to the relay 104. The size of the resistance is selected so as to convert essentially all of the kinetic energy of the motor into heat for dissipation through the resistor 112 when relay 104 turns the motor off.

Figure 5:
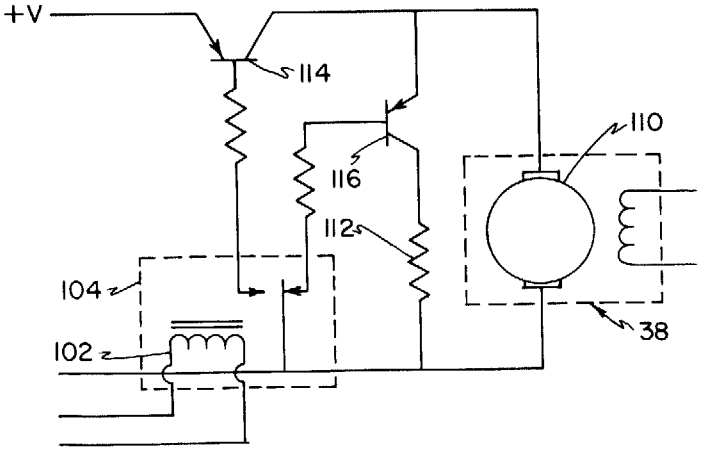

While the embodiment illustrated in FIG. 4 has been found to operate satisfactorily, the start-stop frequency of the motor has been found to be as much as 30 to 60 times a minute. Because the armature current passing through the relay is quite high, the relay 104 has been found to wear out quite rapidly. In order to extend the operating life of the relay, the embodiment of FIG. 5 was developed. The circuit embodiment of FIG. 5 differs from the embodiment of FIG. 4 principally in that transistors 114 and 116 are used to switch the motor 38 off and on, respectively. The transistors reduce the actual amount of current passing through the relay 104 so as to preserve the life of the relay.

The Method of the FIG. 1 Embodiment

Having described the apparatus of FIG. 1, the method of dialyzing a patient's blood with a single venipuncture will now be described.

Initially, the set points on the pressure monitor 70 are adjusted by moving the markers 88, 90 and 92 to represent the desired venous high and low pressures and the desired arterial low pressure, respectively. The arterial and venous lines are primed by filling the lines with isotonic saline. When a single venipuncture or cannulation has been performed, the arterial and venous lines 34 and 62 are filled with blood.

The blood pump 38 is energized so as to force blood through the arterial line toward the dialyzer 60. As has been previously described, when the blood pump 38 is in operation, the solenoid clamp 80 is closed thereby occluding the flow of blood through the venous line 62. Thus, continued rotation of the pump 38 develops an increasing pressure in the venous line 62 above the clamp 80. The increased pressure is communicated through the conductor 66 to the pressure monitor 70. As the indicator 84 progressively advances up the pressure scale on bezel 82, it will be brought into coincidence with marker 88. Advancement of the indicator 84 is concurrent with the elevational rise of the mercury 198 in the mercury column 194 (FIG. 3). When the mercury 198 effectively eliminates light from the source 202 to the photocell 94, the relay driver 102 (FIG. 2) will be de-energized simultaneously opening the solenoid switch 80 and turning the motor 38 off through the circuit illustrated in FIGS. 4 or 5.

When the pump 38 is off, the engaging one of the cylinders 48 or 50 will serve as a clamp to occlude the arterial line 34 and prevent inflow of blood through the cannula 24 and coupling 28. While the pump 38 is stopped, the increased pressure in the venous line 62 is reduced by pushing the blood in venous line 62 through the coupling 28 and catheter 24 again into the blood vessel 22 of the patient. As the pressure in venous line 62 is reduced, the indicator 84 will gradually drop. The time delay in the circuit of FIG. 2 prevents the relay 104 from switching until the selected time interval has been covered.

Thereafter, the solenoid clamp 80 is energized by action of the time delay relay to the illustrated occluded position and the pump 38 is again energized to draw blood from the blood vessel 22 through the cannula 24. In the event the arterial line 34 becomes obstructed such as with a clot or the like, the arterial line pressure in conductor 72 will drop the indicator 86 to the minimum set point at marker 92. When the indicator 86 reaches this low point, the pump 38 will be turned off in order to protect the patient. In the event a coil or membrane in the dialyzer 60 is ruptured, the emergency set point (determined by photocell 208 shown in FIG. 3) will be triggered to shut off both the blood pump and the solenoid 80.

The activation or deactivation of the solenoid, double solenoid or blood pump can either be achieved by letting the pressure travel inbetween two set points or by oscillating around one set point. The latter method (which is preferred) necessitates a time delaying device which prolongs one phase of the cycle. This phase can be chosen either to be a phase of prolonged occlusion or prolonged opening of the solenoid. Regarding the different possibilities described, this will result in prolongation of phases with rising or falling pressures.

In general, in case of coil rupture, the blood pump should stop and the venous solenoid should open (in order to return as much blood to the patient as can be recovered).

Figure 7:
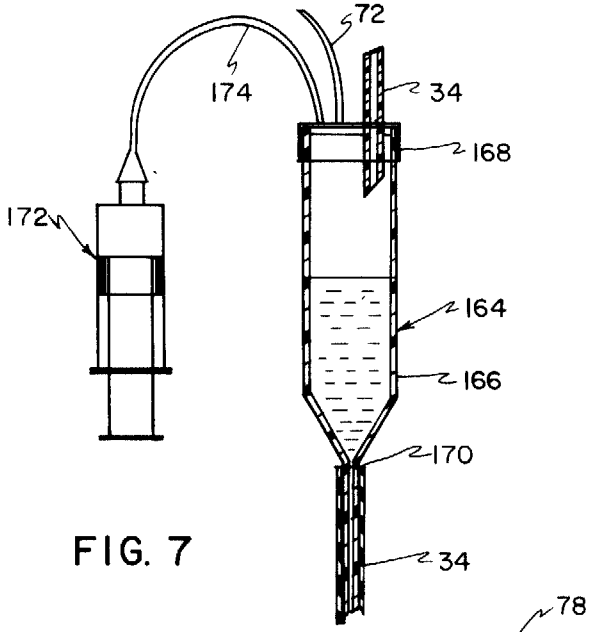
FIG. 7 is a partial cross-section of the flow chamber forming part of the system of FIG. 6.
Figure 6:
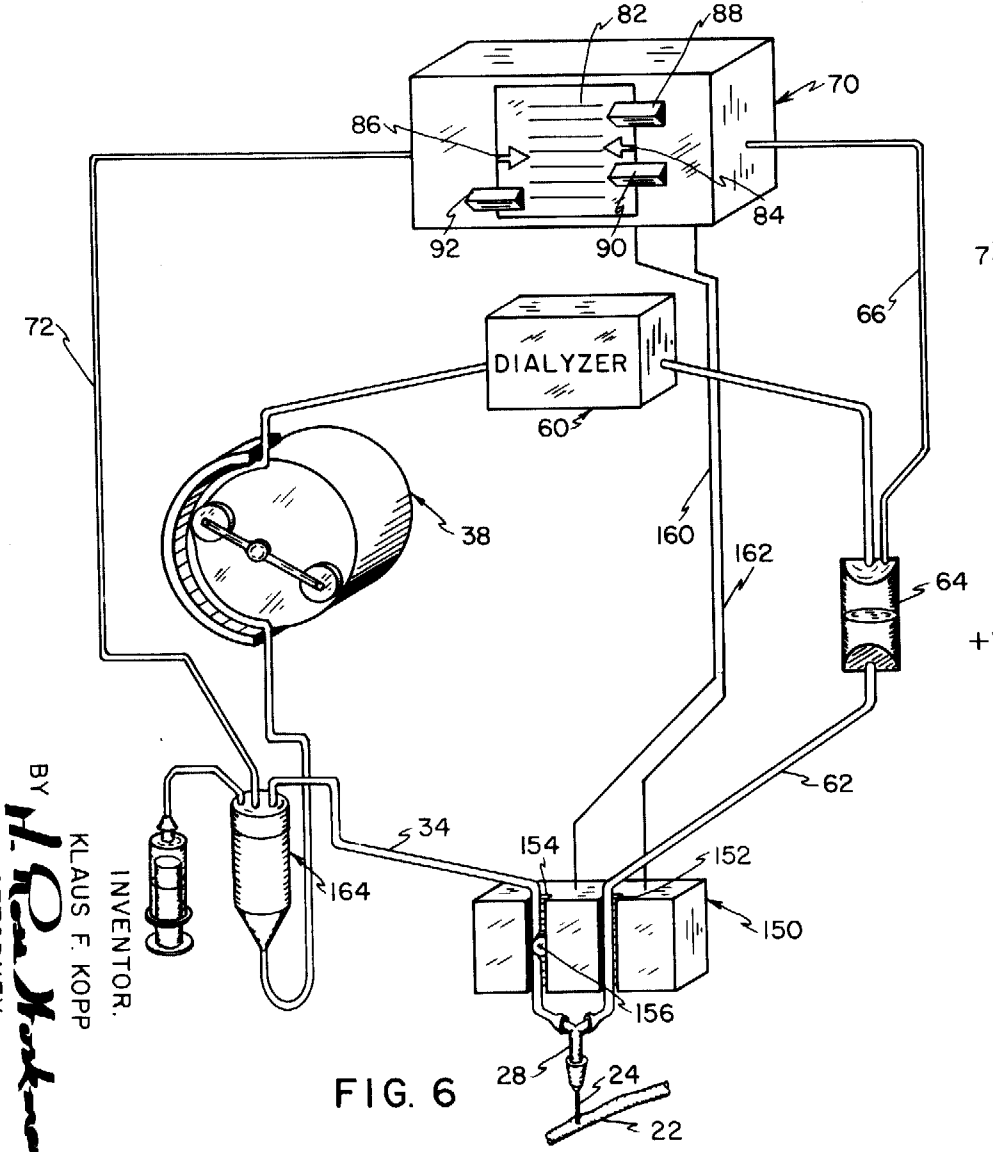
FIG. 6 is a schematic perspective of another presently preferred system for dialyzing a patient's blood using a single venipuncture.

The Embodiment of FIGS. 6 and 7

FIG. 6 illustrates another presently preferred dialyzing system utilizing a single venipuncture. The FIG. 6 embodiment differs from the FIG. 1 embodiment primarily in that the pump 38 is continuously operating and the single solenoid clamp 80 has been replaced by a double solenoid clamp 150. The solenoid clamp 150 has parallel channels 152 and 154 through which the venous and arterial lines 62 and 34, respectively, pass. The solenoid has a detent 156 in each of the channels 152 and 154, the detent 156 being selectively actuated alternately into channel 152 or 154. Control of the detent is provided through electrical conductors 160 and 162 connecting the solenoid clamp 150 to the pressure monitor 70.

Additionally, the system of FIG. 6 has an arterial flow chamber generally designated 164 and more clearly illustrated in FIG. 7. The flow chamber 164 is preferably formed of a rigid cylindrical member 166 which may be formed of plastic and is desirably transparent. The member 166 is fitted with an air-tight cap 168 into which one end of the arterial line 34 is mounted. The member 166 has a downwardly tapered portion and terminates in a male coupling 170. Another portion of the arterial line 34 is press-fit onto the male coupling 170. The cap 168 also serves as a mounting site for pressure-conducting tube 74 and a blood level adjuster generally designated 172. The blood level adjuster may comprise a conventional hypodermic syringe connected to the cap 168 by a plastic tube 174. Where desired, the tube 174 may be clamped to maintain pressure communication through conductor 72.

The Method of FIGS. 6 and 7

The arterial and venous lines 34 and 62 are primed with isotonic saline as described in connection with FIG. 1 above. The pump 38 operates continuously. Assuming that the venous line 62 is occluded by solenoid 150, blood is withdrawn from the patient's blood vessel 22 through the cannula 24 and arterial line 34 into the arterial flow chamber 164. The blood is then pumped out of the arterial flow chamber to the dialyzer 60. Continued pumping by the pump 38 causes the pressure in the venous line 62 to increase because of the occlusion in the channel 152. As the pressure rises, the indicator 84 will rise to the set point determined by marker 88. When the set point is reached, solenoid 150 will be actuated to open the venous line 62 and to occlude, simultaneously, the arterial line 34. The high pressure in the venous line 62 will then cause the blood therein to flow through the adapter 28, cannula 24 and into the blood vessel 22.

Referring again to FIG. 7, the continued operation of the blood pump 38 causes blood to flow out of the arterial flow chamber thereby decreasing the pressure in the member 166, the decreased pressure being communicated through line 72 to the pressure monitor 70. When the time which has been preset by the time delay relay has elapsed, the pressure monitor 70 will again actuate the solenoid clamp 150 to close the venous line 62 and open the arterial line 34. Blood will again be drawn from the patient through the arterial line 34 to replenish the reservoir in the arterial flow chamber 164 and also to conduct the blood through the dialyzer 60 as the cycle is again commenced.

From the foregoing, it can be appreciated that effective dialysis of a patient's blood can be obtained with a single venipuncture. Moreover, it has been found that the small amounts of blood which are recycled through the system at the adapter 28 do not unfavorably influence the efficiency. A surprising amount of the blood is withdrawn from the patient and again injected into the patient with each cycle in the system. Moreover, it has been found that a patient's dialysis time using the single venipuncture method is only slightly increased if at all, in most cases, over the prior art double venipuncture method.

Figure 8:
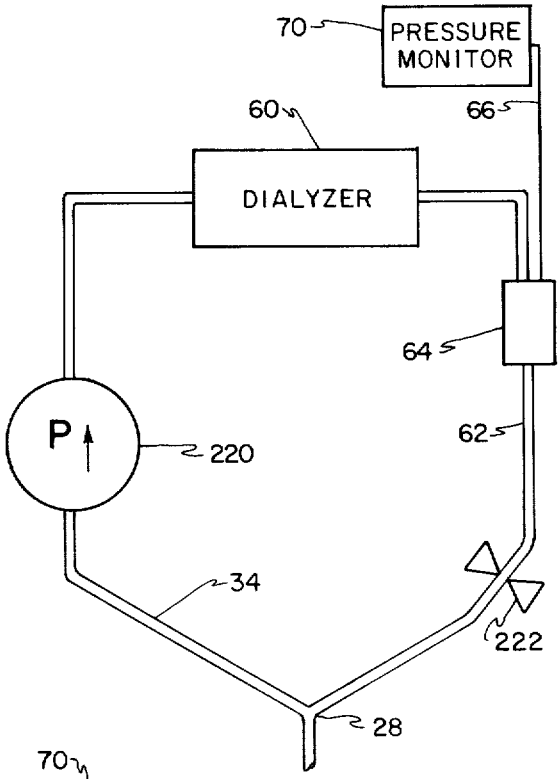
FIGS. 8 and 9 are schematic diagrams of still other presently preferred method embodiments of the invention.
Figure 9:
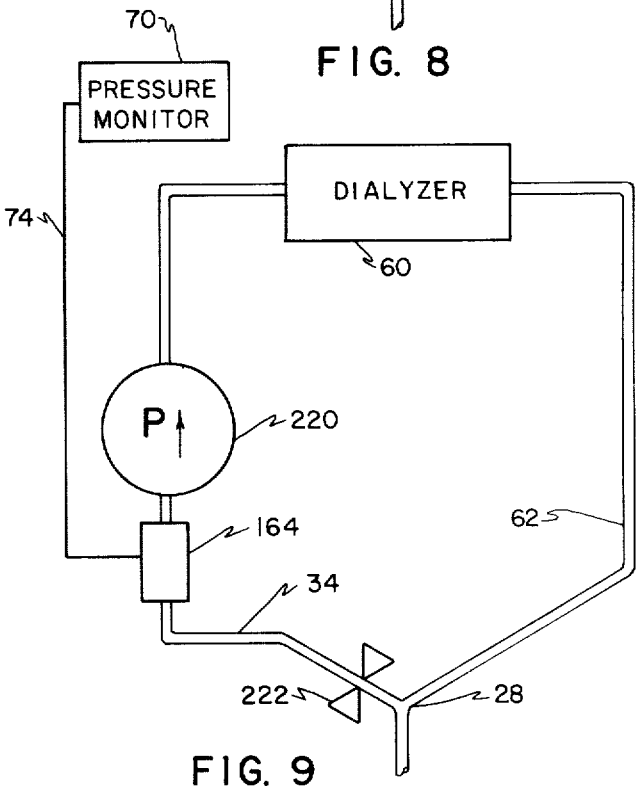

The Embodiments of FIGS. 8 and 9

The embodiments of FIGS. 8 and 9 maximize the tendency of the blood to "short-circuit" at the bifurcated coupling 28. In this embodiment, a substantial portion of the blood is intentionally recirculated a plurality of times through the arterial line 34, the dialyzer 60 and the venous line 62. A suitable blood pump 220 continually operates at a comparatively high rate of speed so that the blood is forced through the dialyzer, venous and arterial lines at the rate of approximately 300 to 400 milliliters per minute. As can be appreciated, this flow rate is approximately twice as great as the flow rate from the patient through a dialyzer in the systems of FIGS. 1 and 6.

In order to dialyze the patient's blood, only a single clamp 222 is necessary. In FIG. 8, clamp 222 is located in the venous line 62 below the bubble trap 64. Alternatively, as shown in FIG. 9, the clamp 222 may be disposed in the arterial line 34 beneath the arterial flow chamber 164.

In the method embodiment of FIG. 8, the system is primed with saline as above described and blood is gradually drawn into the arterial line 34 as will now be more particularly described. When the clamp 222 is in the closed or occluding position, the pump 220 will continue to draw blood from the patient and force the blood in the arterial line 34 through the dialyzer 60. Thus, a pressure will develop in the venous line 62, said pressure being conducted through line 66 and monitored by the pressure monitor 70. When the pressure reaches a predetermined high set point, the clamps 222 will be activated to the open position. At that moment, the pressure in the venous line will be greater than the pressure in the arterial is equalized by displacing one volume of dialyzed blood into the patient and another volume of dialyzed blood again into the arterial line 34.

After a particular predetermined time period has elapsed or, as soon as the pressure in line 66 has dropped to a predetermined level, the clamp 222 will again occlude the venous line 62 to develop pressure above the clamp 222. It is observed that as soon as the clamp 222 is closed, a vacuum is developed in the arterial line 34 below the pump 220. This vacuum is filled by drawing blood from the patient into the arterial line 34. When the pressure in line 66 reaches the predetermined set point in the monitor 70, the clamp 222 is again opened and the blood under pressure in the venous line 62 will be forced toward the bifurcated coupling 28. Because the line 34 has been filled with blood while the clamp 222 was closed, a substantial portion of the blood under pressure in the venous line 62 will be forced through the coupling 28 into the patient.

An alternative to the described method of embodiment is illustrated in FIG. 9. In FIG. 9, the clamp 222 is located in the arterial branch 34 beneath the flow chamber 164. The pump 222 is in continual operation at a comparatively high flow rate, similar to that described above so that a flow rate of approximately 300 to 400 millimeters per minute exists in the system. When the clamp is closed, blood will be forced by the pump 220 through the dialyzer 60 and venous line 62 so that the blood is forced into the patient through the bifurcated coupling 28. Continued pumping with the clamp 222 closed causes the pressure in the chamber 164 to be reduced, said pressure reduction being reflected through conductor 74 and monitored in the pressure monitor 70. When the pressure in monitor 70 reaches predetermined low set point, clamp 222 will open thereby allowing the pump 220 to draw blood from the patient through the bifurcated coupling 28 and the venous line 62. The volume of blood required to equalize the pressure is greater than can be supplied from venous line 62 so that a substantial volume of blood is drawn from the patient.

The embodiments of FIGS. 8 and 9 have been found to provide some unusually valuable advantages over other types of dialysis systems. For example, the very high flow rate causes much turbulence in the dialyzer which breaks up the boundary layers normally existing in the dialyzer thereby substantially increasing diffusion across the membrane. Moreover, inasmuch as flow through the dialyzer is normally laminar, the turbulence developed by the high flow rate causes the erythrocytes to have a brushing effect against one another and against the membrane to further increase the rate of dialysis.

Inasmuch as a substantial portion of the blood in the system is circulated through the dialyzer a plurality of times before being reinjected into the patient, the blood normally in the extracorporeal system has an unusually low concentration of waste substances. Thus, when blood is drawn from the patient into the system, there is blood-to-blood diffusion as the infusing blood is mixed with the recirculating blood in the system. It has been found that the method set forth in FIGS. 8 and 9 achieves a surprisingly high dialysis efficiency.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of dialyzing the blood of a patient with a single cannula dialysis system having a dialyzer, a blood pump acting thereon and openable clamp comprising the steps of:

cannulating the patient by placing a single cannula into the bloodstream of the patient;

providing an extracorporeal bifurcated flow path in communication with the cannula, the flow path having an arterial branch, a venous branch and the blood dialyzer interposed therebetween;

continuously pumping the blood in the arterial branch toward the dialyzer with a pump acting upon the arterial branch;

creating two pressure zones by situating the openable clamp along the length of the venous branch, the first pressure zone defined by the portion of the flow path downstream from the pump and upstream from the clamp so as to include the dialyzer and the second pressure zone being defined by the portion of the flow path upstream from the pump and downstream from the clamp so as to include the patient cannula;

developing increased pressure in the first zone and simultaneously decreasing pressure in the second zone by closing the clamp and continuously pumping blood in the arterial line so as to draw blood from the patient; and thereafter equalizing the pressure between the zones by opening the clamp thereby permitting blood to be transferred to the patient.

2. A method of dialyzing the blood of a patient with a single cannula dialysis system having a dialyzer, a blood pump acting thereon and openable clamp comprising the steps of:

cannulating the patient by placing a single cannula into the bloodstream of the patient;

providing an extracorporeal bifurcated flow path in communication with the cannula, the flow path having an arterial branch, a venous branch and the blood dialyzer interposed therebetween;

continuously pumping the blood in the arterial branch toward the dialyzer with a pump acting upon the arterial branch;

creating two pressure zones by situating the openable clamp in the arterial line upstream from the pump, the first pressure zone being defined by the portion of the flow path downstream from the pump and upstream from the clamp so as to include both the patient cannula and the dialyzer and the second pressure zone being defined by the portion of the flow path upstream from the pump and downstream from the clamp;

developing increased pressure in the first zone by continuously pumping the blood while closing the clamp thereby increasing the pressure in the first zone to inject blood into the patient; and equalizing the pressure between the zones by opening the clamp and permitting blood to be transferred from the patient to the flow path.

*3. A method of dialyzing the blood of a patient with a single cannulation in a system including a pump and a hemodialyzer connected together in a series configuration, and a single hollow cannula having a bifurcated conduit connected thereto to provide an arterial branch and a venous branch, coupled respectively to opposed ends of the series connected pump and hemodialyzer, wherein the interconnected conduit, pump and hemodialyzer define a closed system connected to the single hollow cannula, comprising the steps of:*

*cannulating the blood vessel of a patient with the single cannula through which blood is withdrawn from and returned to the patient through said system in alternate phases of successive cycles of operation;*

*pumping blood from the patient to the hemodialyzer through the arterial branch, while preventing the return of blood to the patient through the venous branch;*

*sensing pressure in the closed system;*

*automatically occluding blood flow through the arterial branch to stop the withdrawal of blood from the patient in response to the sensing of a predetermined first pressure level in the closed system, while permitting the return of blood to the patient through the venous branch; and, alternately,*

*automatically occluding blood flow through the venous branch to stop the return flow of blood to the patient in response to the sensing of a predetermined second pressure level in the closed system, while permitting blood withdrawal from the patient through the arterial branch, so that blood is alternately withdrawn and returned to the patient in alternate phases of each successive cycle of operation of the system in response to the sensing of the predetermined first and second pressure levels.*

*4. A method of dialyzing the blood of a patient with a single cannulation in a system including a pump and a hemodialyzer connected together in a series configuration, and a single hollow cannula having a bifurcated conduit connected thereto to provide an arterial branch and a venous branch, coupled respectively to opposed ends of the series connected pump and hemodialyzer, wherein the interconnected conduit, pump and hemodialyzer define a closed system connected to the single hollow cannula, comprising the steps of:*

*cannulating the blood vessel of a patient with the single cannula through which blood is withdrawn from and returned to the patient in alternate phases of successive cycles of operation;*

*pumping blood from the patient to the hemodialyzer through the arterial branch, while preventing the return of blood to the patient through the venous branch;*

*sensing pressure in the closed system downstream of the pump;*

*automatically occluding blood flow through the arterial branch to stop the withdrawal of blood from the patient in response to the sensing of a predetermined first pressure level in the closed system, while permitting the return of blood to the patient through the venous branch; and, alternately,*

*automatically occluding blood flow through the venous branch to stop the return flow of blood to the patient in response to the sensing of a predetermined second pressure level in the closed system, wherein the first pressure level is higher than said second level, while permitting blood withdrawal from the patient through the arterial branch, so that blood is alternately withdrawn and returned to the patient in alternate phases of each successive cycle of operation of the system in response to the sensing of the predetermined first and second pressure levels.*

* * * * *

UNITED STATES PATENT AND TRADEMARK OFFICE

CERTIFICATE OF CORRECTION

PATENT NO. : RE. 29,346

DATED : August 9, 1977

INVENTOR(S) : KLAUS F. KOPP

It is certified that error appears in the above-identified patent and that said Letters Patent are hereby corrected as shown below:

Column 5, line 60, delete "16" and insert --196--.

Column 9, line 52, after "arterial" insert --line and in the patient's blood stream. The pressure--.

Signed and Sealed this

*Eighteenth* Day of *April 1978*

[SEAL]

*Attest:*

RUTH C. MASON
*Attesting Officer*

LUTRELLE F. PARKER
*Acting Commissioner of Patents and Trademarks*